United States Patent [19]
Holt et al.

[11] Patent Number: 5,527,806
[45] Date of Patent: Jun. 18, 1996

[54] 17α AND 17β SUBSTITUTED ACYL 4 AZA STEROIDS

[75] Inventors: Dennis A. Holt, Stow, Mass.; Mark A. Levy, Wayne; Hye-Ja Oh, Cheltenham, both of Pa.

[73] Assignee: SmithKline Beecham Corporation, Philadelphia, Pa.

[21] Appl. No.: 338,563

[22] Filed: Nov. 21, 1994

[30] Foreign Application Priority Data

May 21, 1992 [GB] United Kingdom .................. 9210880

[51] Int. Cl.$^6$ ............................................... A61K 31/58
[52] U.S. Cl. ............................................ 514/284; 546/77
[58] Field of Search ................................. 514/284; 546/77

[56] References Cited

U.S. PATENT DOCUMENTS

| | | | |
|---|---|---|---|
| 4,377,584 | 3/1983 | Rasmusson et al. | 546/77 |
| 4,760,071 | 7/1988 | Rasmusson et al. | 546/77 |
| 4,859,681 | 8/1989 | Rasmusson et al. | 546/77 |
| 4,882,319 | 11/1989 | Holt et al. | 514/119 |
| 4,888,336 | 12/1989 | Holt et al. | 514/284 |
| 4,910,226 | 3/1990 | Holt et al. | 514/573 |
| 5,049,562 | 9/1991 | Rasmusson et al. | 546/77 |
| 5,110,939 | 5/1992 | Holt et al. | 548/250 |
| 5,116,983 | 5/1992 | Bhattacharya et al. | 546/77 |
| 5,120,742 | 6/1992 | Rasmusson et al. | 546/77 |
| 5,304,562 | 4/1994 | Biollaz | 546/77 |

FOREIGN PATENT DOCUMENTS 0200859  12/1986  European Pat. Off. .

OTHER PUBLICATIONS

Chem. Abs. 1992 vol. 118 No. 21 Abs. No. 213352h and No. 11 Abs. No. 102309e.
Back et al. J. Org. Chem, 54, pp. 1904–1910, 1989.
Brooks Steroids, 47, pp. 1–19, 1986.
Doorenbos J. Pharmaceutical Sciences, vol. 60, No. 8 pp. 1234–1235 1971.
J. Pharmaceutical Sciences, vol. 62, No. 4 pp. 638–640 1973.
Rasmusson et al. J. Med. Chem. 27, pp. 1690–1701 1984.
Back J. Org. Chem, 46, pp. 1442–1446 1981.
Rasmusson J. Med. Chem, 29, pp. 2298–2315 1986.
Diani J. Clinical Endocrinology and Metabolism, vol. 74, No. 2, pp. 345–350.

*Primary Examiner*—Donald G. Daus
*Attorney, Agent, or Firm*—Wayne J. Dustman; Stephen Venetianer; Edward T. Lentz

[57] ABSTRACT

Invented are 17β-substituted acyl-4-aza analogues of steroidal synthetic compounds, pharmaceutical compositions containing these compounds, and methods for using these compounds to inhibit steroid 5-α-reductase. Also invented are intermediates and processes used in preparing these compounds.

5 Claims, No Drawings

17α AND 17β SUBSTITUTED ACYL 4 AZA STEROIDS

FIELD OF THE INVENTION

The present invention relates to certain novel 17α and 17β-substituted acyl 4-aza steroidal compounds, pharmaceutical compositions containing these compounds, and methods for using these compounds to inhibit steroid 5-α-reductase. Also invented are novel intermediates and processes useful in preparing these compounds.

DESCRIPTION OF RELATED ART

The class of steroidal hormones known as androgens is responsible for the physical characteristics that differentiate moles from females. Of the several organs that produce androgens, the testes produce these hormones in the greatest amounts. Centers in the brain exert primary control over the level of androgen production. Numerous physical manifestations and disease states result when ineffective control results in excessive androgen hormone production. For example, acne vulgaris, seborrhea, female hirsutism, male pattern baldness and prostate diseases such as benign prostatic hypertropy are correlated with elevated androgen levels. Additionally, the reduction of androgen levels has been shown to have a therapeutic effect on prostate cancer.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue, in these tissues but not in others such as muscle and testes. Steroid 5-α-reductase is a Nicotinamide Adenine dinucleotide Phosphate(NADPH)dependent enzyme that converts testosterone to DHT. The importance of this enzyme in male development was dramatically underscored by discovery of a genetic steroid 5-α-reductase deficiency in male pseudohermaphrodites. Imperator-McGinley, J., et al., (1979), *J. Steroid Biochem.* 11:637–648.

A number of steroidol 4-aza 5-α-reductase inhibitors are known in the art. For example, 1. U.S. Pat. No. 4,888,336, to Holt et al. describes Steroidal 4-aza derivatives as useful 5-α-reductase inhibitors;

2. U.S. Pat. No. 4,377,584, to Rasmusson et al. describes steroidal 4-aza derivatives as useful 5-α-reductase inhibitors;

3. *TIPS* (December 1989) Vol. 10, pp. 491–495, by B. W. Metcalf, et al., describes the effect of inhibitors of steroid 5α reductase in benign prostatic hyperplasia, male pattern baldness and acne.

However, none of the above references specifically suggest that any of the novel steroidal 17α or 17β-substituted acyl-4-aza compounds of the present invention would have utility as potent testosterone 5-α-reductase inhibitors.

SUMMARY OF THE INVENTION

This invention relates to a compound of the formula I:

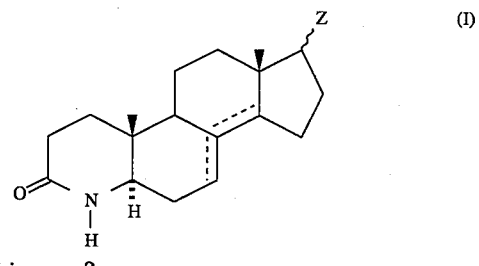

wherein Z is α or β

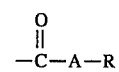

in which
either the B ring has a double bond where inidcated by the broken line or the C ring has a double bond where indicated by the broken line; A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$,
where
R$^6$ is hydrogen or alkyl,
n is 0–2 and
R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; b) cycloalkyl is nonaromatic, unsaturated or saturated, cyclic or polycyclic C$_3$–C$_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH,
where
R$^6$ is hydrogen or alkyl,
n is 0–2,
R$^7$ is hydrogen or alkyl and
R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; and c) aryl is cyclic or polycyclic aromatic C$_3$–C$_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates and solvates thereof.

The invention also is a method for inhibiting 5-α-reductase activity in mammals, including humans, that comprises administering to a subject an effective amount of a presently invented 5-α-reductase inhibiting compound. In a further aspect of the invention there are provided novel intermediates and novel processes useful in preparing the presently invented 5-α-reductase inhibiting compounds. Included in the present invention are pharmaceutical compositions comprising a pharmaceutical carrier and compounds useful in the methods of the invention. Also included in the present invention are methods of co-administering the presently invented 5-α-reductase inhibiting compounds with further active ingredients.

DETAILED DESCRIPTION OF THE INVENTION

The compounds of this invention that inhibit 5-α-reductase have the following Formula (I):

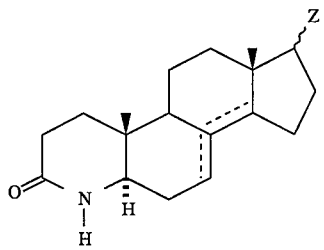

wherein Z is α or β

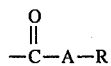

in which either the B ring has a double bond where inidcated by the broken line or the C ring has a double bond where indicated by the broken line; A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where $R^6$ is hydrogen or alkyl, n is 0–2 and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, $C_6$–$C_{12}$aryl, substituted $C_6$–$C_{12}$aryl and protected-OH, where $R^6$ is hydrogen or alkyl, n is 0–2 and $R^7$ is hydrogen or alkyl;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting off alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates and solvates thereof.

Preferred among the presently invented compounds are those having the following Formula (II):

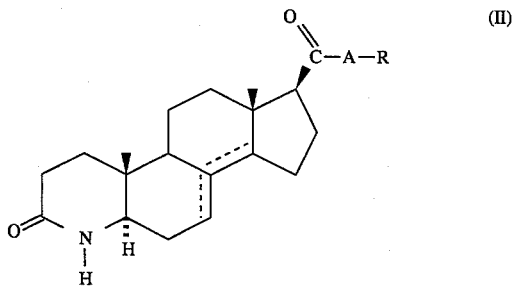

(II)

in which
either the B ring has a double bond where inidcated by the broken line or the C ring has a double bond where indicated by the broken line; A is absent or present as a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$,
where
$R^6$ is hydrogen or alkyl,
n is 0–2 and
$R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH,
where
$R^6$ is hydrogen or alkyl,
n is 0–2,
$R^7$ is hydrogen or alkyl and
$R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting off alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting off aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting off alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH,
where
$R^6$ is hydrogen or alkyl,
n is 0–2,
$R^7$ is hydrogen or alkyl and
$R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates and solvates thereof.

Preferred among the presently invented Formula II compounds are those having the following Formula (III):

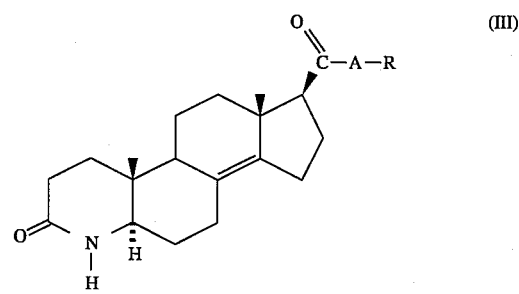

(III)

in which A and R are as defined in Formula (II); and pharmaceutically acceptable salt, hydrates and solvates thereof.

Preferred among the presently invented Formula III compounds are those in which A is absent or present as a linear or branched, saturated or unsaturated hydrocarbon chain containing from 1–6 carbon atoms and R is a) a linear or branched, saturated or unsaturated hydrocarbon chain containing 1–12 carbon atoms substituted with one or more substituents selected from the group consisting of: —OC$_6$–C$_{12}$aryl, carboxy, —OC$_1$–C$_4$alkyl, halogen and —S(O)$_n$R$^7$, where n is 0–2 and $R^7$ is hydrogen or $C_{1-4}$ alkyl;

b) $C_3$–$C_8$ nonaromatic, unsaturated or saturated, cycloalkyl, optionally substituted with one or more substituents selected from the group consisting of: —OC$_6$–C$_{12}$aryl, —(CH$_2$)$_m$OH, —OC$_1$–C$_4$alkyl, $C_6$–$C_{12}$aryl, $C_1$–$C_4$alkyl, trifluoromethyl, halogen, —(CH$_2$)$_p$COOH, —S(O)$_n$R$^7$ and protected —OH, where m is 0–4, p is 0–3, n is 0–2 and $R^7$ is hydrogen or $C_{1-4}$alkyl; or c) $C_4$–$C_{12}$aryl, optionally containing one or more heteroatoms, provided that when C is 4 the aromatic ring contains at least one heteroatom, and optionally substituted with one or more substituents selected from the group consisting of: —OC$_6$–C$_{12}$aryl, —(CH$_2$)$_m$OH, $C_6$–$C_{12}$aryl, $C_1$–$C_4$alkyl, —OC$_1$–C$_4$alkyl, trifluoromethyl, halogen, —(CH$_2$)$_p$COOH, —S(O)$_n$R$^7$ and protected —OH, where m is 0–4, p is 0–3, n is 0–2 and $R^7$ is hydrogen or $C_{1-4}$alkyl; and pharmaceutically acceptable salts, hydrates and solvates thereof.

Particularly preferred among Formula III compounds are those in which A is absent or present as a linear or branched, saturated or unsaturated hydrocarbon chain containing from 1–4 carbon atoms and R is a) $C_3$–$C_8$ nonaromatic, unsaturated or saturated cycloalkyl, optionally substituted with one or more substituents selected from the group consisting of: halogen, thio, methylsulfonyl, methylsulfoxyl, methylthio, carboxy, hydroxy, trifluoromethyl, phenoxy and methoxy or b) $C_4$–$C_{12}$ aryl, optionally containing one more heteroatoms, provided that when C is 4 the aromatic ring contains at least one heteroatom, and optionally substituted with one or more substituents selected from the group consisting of: halogen, thio, methylsulfonyl, methylsulfoxyl, methylthio, carboxy, hydroxy, trifluoromethyl, phenoxy and methoxy and pharmaceutically acceptable salts, hydrates and solvates thereof.

Particularly preferred among Formula III compounds are those in which A is absent or present as a linear or branched, saturated or unsaturated hydrocarbon chain containing from 1–4 carbon atoms and R is a) $C_5$–$C_7$ cycloalkyl or b) $C_4$–$C_{12}$ aryl, optionally containing one or more heteroatoms, provided that when C is 4 the aromatic ring contains at lease one heteroatom, and optionally substituted with one or more substituents selected from the group consisting of: halogen, thio, methylsulfonyl, methylsulfoxyl, methylthio, carboxy, hydroxy, trifluoromethyl, phenoxy and methoxy and pharmaceutically acceptable salts, hydrates and solvates thereof.

Particularly preferred is the Formula (III) compound in which A is absent and R is phenyl.

The term "α", as used herein, follows standard chemical terminology and means down or that the corresponding substituent is attached below the plane of the paper.

The term "β", as used herein, follows standard chemical terminology and means up or that the corresponding substituent is attached above the plane of the paper.

By the term "protected hydroxy" or "protected —OH" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like. As used herein $C_x$–$C_y$ is meant a moiety having from x to y carbons.

By the term "aryl" as used herein, unless otherwise defined, is meant cyclic or polycyclic aromatic $C_3$–$C_{12}$, optionally containing one or more heteroatoms, provided that when C is 3 the aromatic ring contains at least two heteroatoms and when C is 4 the aromatic ring contains at least one heteroatom, and optionally substituted with one or more substituents selected from the group consisting of: alkyl, $C_6$–$C_{12}$ aryl, substituted cycloalkyl, substituted $C_6$–$C_{12}$aryl, aryloxy, hydroxy, alkoxy, cycloalkyl, acyloxy, amino, N-acylamino, nitro, cyano, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen, and protected —OH, where R$^6$ is hydrogen or alkyl, n is 0–2, R$^7$ is hydrogen or alkyl and R$^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl.

Examples of aryl and substituted aryl substituents as used herein include: phenyl, naphthyl, furanyl, biphenyl, hydroxyphenyl, pyridyl, fluorophenyl, dihydroxyphenyl, methylenedioxyphenyl, dimethylhydroxyphenyl, methoxyphenyl, trifluoromethylphenyl carboxymethylphenyl, phenoxyphenyl, methylsulfonylphenyl, methylthiophenyl, difluorophenyl, carboxyphenyl, methylsulfoxylphenyl and thiophenyl.

Preferred examples of aryl and substituted aryl substituents as used herein include: phenyl, 4-fluorophenyl, 1-naphthyl, 4-biphenyl, 4-methoxyphenyl, 4-phenoxyphenyl, 4-trifluoromethylphenyl, 4-methylsulfonylphenyl, 4-methylthiophenyl, 3,5-difluorophenyl, 4-hydroxyphenyl, 4-carboxyphenyl, 2-furanyl, 4-methylsulfoxylphenyl, 3-thiophenyl, 2-pyridyl, 3-pyridyl, 4-pyridyl and 3,4-methylenedioxyphenyl.

By the term "$C_6$–$C_{12}$ aryl" as used herein, unless otherwise defined, is meant phenyl, naphthyl, 3,4-methylenedioxyphenyl, or biphenyl.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —(CH$_2$)$_g$C(O)OR$^6$, —S(O)$_n$R$^7$, nitro, cyano, halogen, trifluoromethyl and protected —OH, where g is 0–6, R$^6$ is hydrogen or alkyl, n is 0–2, and R$^7$ is hydrogen or alkyl.

By the term "alkoxy" as used herein is meant -Oalkyl where alkyl is as described herein including —OCH$_3$ and —OC(CH$_3$)$_2$CH$_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —OC(O)CH$_3$, —OC(O)CH(CH$_3$)$_2$ and —OC(O)(CH$_2$)$_3$CH$_3$.

By the term "N-acylamino" as used herein is meant —N(H)C(O)alkyl, where alkyl is as described herein. Examples of N-acylamino substituents as used herein include: —N(H)C(O)CH$_3$, —N(H)C(O)CH(CH$_3$)$_2$ and —N(H)C(O)(CH$_2$)$_3$CH$_3$.

By the term "aryloxy" as used herein is meant —OC$_6$–C$_{12}$aryl where C$_6$–C$_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifluoromethyl, acyloxy, amino, N-acylamino, hydroxy, —(CH$_2$)$_g$C(O)OR$^6$, —S(O)$_n$R$^7$, nitro, cyano, halogen and protected —OH, where g is 0–6, R$^6$ is hydrogen or alkyl, n is 0–2 and R$^7$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$–$C_{12}$ carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$ and —$CH(CH_3)$—$CH_2$—$CH_3$, —$CH$=$CH_2$.

By the term "treating" and derivatives thereof as used herein, is meant prophylatic or therapeutic therapy.

Compounds of Formula (I) and compounds of the formula (V) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The term "a-receptor antagonist", as used herein, refers to a known class of alpha-andrenergic receptor antagonist comounds, such as described in Lafferty, et al. U.S. Pat. No. 4,963,547, which are utilized in treating vascular disorders such as diabetes, cardiovascular disease, benign prostatic hypertrophy and ocular hypertension. Preferred alpha-andrenergic receptor antagonists for use in the compositions and methods of the invention include amsulosin, terazosin, doxazosin, alfuzosin, indoramin, prazosin and 7-chloro-2-ethyl-3,4,5,6-tetrahydro- 4-methylthieno[4,3,2-ef][3]-benzazepine.

By the term "amsulosin" as used herein is meant a compound of the formula

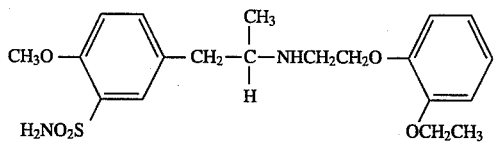

and salts, hydrates and solvates thereof.

Chemically, amsulosin is designated as (—)—(R)—5—2-[[2—(O-ethoxyphenoxy)ethyl]amino]propyl]-2-methoxybenzenesulfonamide.

Amsulosin is disclosed in U.S. Pat. No. 4,703,063 and claimed in U.S. Pat. No. 4,987,125 as being useful in treating lower urinary tract dysfunction.

By the term "terazosin" as used herein is meant a compound of the formula

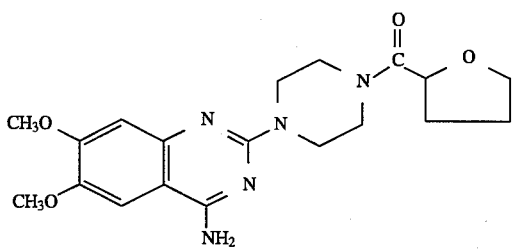

and salts, hydrates and solvates thereof.

Chemically, terazosin is designated as 1-(4-amino-6,7-dimethoxy-2 quinazolinyl)-4-[(tetrahydro-2-furoyl)carbonyl]piperazine. Terazosin is disclosed in U.S. Pat. No. 4,251,532.

By the term doxazosin as used herein is meant a compound of the formula

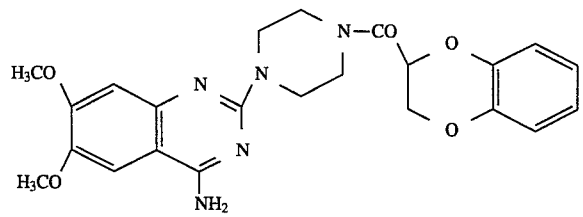

and salts, hydrates and solvates thereof.

Chemically "doxazosin" is designated as 1-(4-amino-6,7-dimethoxy- 2-quinazolinyl)-4-[(2,3-dihydro-1,4-benzodioxin-2-yl)carbonyl]-piperazine.

Doxazosin is disclosed in U.S. Pat. No. 4,188,390.

By the term "alfuzosin" as used herein is meant a compound of the formula

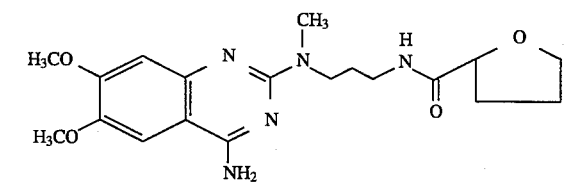

and salts, hydrates and solvates thereof.

Chemically alfuzosin is designated as N-[3-[(4-amino-6,7-dimethoxy- 2-quinazolinyl)methylamino]propyl]tetrahydro-2-furancarboxamide.

Alfuzosin is disclosed in U.S. Pat. No. 4,315,007.

By the term "indoramin" as used herein is meant a compound of the formula

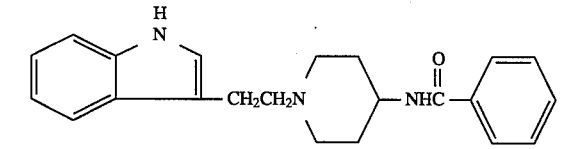

and salts, hydrates and solvates thereof.

Chemically indoramin as designated N-[[1-[2-(1H-indol-3-yl) ethyl]-4-piperidinyl]benzamine.

Indoramin is disclosed in U.S. Pat. No. 3,527,761.

By the term "prazosin" as used herein is meant a compound of the formula

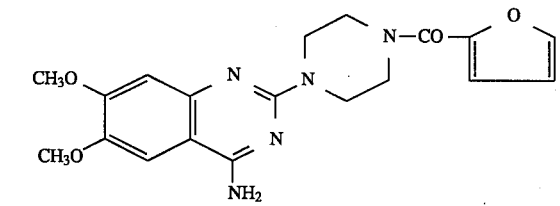

and salts, hydrates and solvates thereof.

Chemically prazosin is designated as 1-(4-amino-6,7-dimethoxy-2-quinazolinyl)- 4-(2-furanylcarbonyl)piperazine.

Prazosin is disclosed in U.S. Pat. No. 3,511,836.

"7-chloro-2-ethyl-3,4,5,6-tetrahydro-4-methylthieno[4,3, 2-ef]-benzazepine" as used herein is meant a compound of the structure

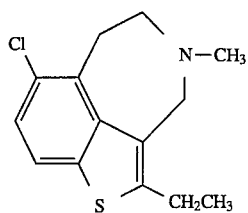

and salts, hydrates and solvates thereof.

7-chloro-2-ethyl-3,4,5,6-tetrahydro-4-methylthieno[4,3,2-ef]-[3]benzazepine is disclosed in U.S. Pat. No. 5,006,521. Additionally, all compounds disclosed in U.S. Pat. No. 5,006,521 as alpha-adrenergic receptor antagonist are preferred alpha-adrenergic receptor antagonist as used herein.

Persons skilled in the art can readily determine if a compound other than one specifically referred to herein is a alpha-andrenergic receptor antagonist by utilizing the assay described in Lafferty I. Thus, all such compounds are included within the scope of the term "alpha-andrenergic receptor antagonist" as used herein.

By the term "minoxidil" as used herein is meant the compound of the formula:

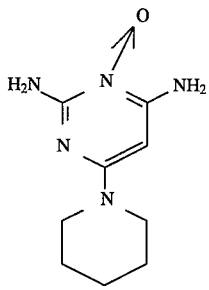

chemically minoxidil is designated as 2,4-pyrimidineadiamine, 6-(1-piperidinyl)-, 3-oxide. Minoxidil is the active ingredient in Rogaine® which is sold as topical solution for stimulating hair growth by the Upjohn Compnay, Kalamazoo, Mich.

The term "aromatase inhibitor", as used herein, refers to a known class of compounds, steroidal and non-steroidal, which prevent the conversion of androgens to estrogens, such as described in Gormley et al. International Publication Number WO 92/18132. Aromatase inhibitors are disclosed in Gormley et al. as having utility in treating benign prostatic hyperplasia when used in combination with a 5-α-reductase inhibitor.

A preferred aromatase inhibitor for use in the compositions and methods of the invention 4-(5,6,7,8-tetrahydroimidazo-[1,5-α]pyridin-5-yl)benzonitrile (fadrazole). Fadrazole is disclosed in U.S. Pat. No. 4,728,645. Additionally, all compounds disclosed in Gormley, et al. International Publication No. WO 92/18132 as having aromatase inhibiting activity are preferred aromatase inhibitors as used herein.

As used herein, when a 5-α-reductase inhibitor, as described herein and a further active ingredient or ingredients are utilized together, said 5-α-reductase inhibitor can be co-administered with said further active ingredient or ingredients.

By the term "co-administering" and derivatives thereof as used herein is meant either simultaneous administration or any manner of separate sequential administration of a 5-α-reductase inhibiting compound, as described herein, and a further active ingredient or ingredients, such as other compounds known to treat the disease states of acne vulgaris, seborrhea, female hirsutism, male pattern baldness, benign prostate hypertrophy or prostatic adenocarcinoma or compounds known to have utility when used in combination with 5-α-reductase inhibitors. Preferably, if the administration is not simultaneous, the compounds are administered in a close time proximity to each other. Furthermore, it does not matter if the compounds are administered in the same dosage form, e.g. one compound may be administered topically and another compound may be administered orally.

Formula (II) compounds are prepared as shown in Schemes I and II wherein A is as described in Formula (II). As used in the specification and in the claims $R^8$ is R or moieties which can be converted to those of R by chemical reactions readily is known to those of skill in the art, such as described in Derek Barton and U. D. Ollis, Comprehensive Organic Chemistry: The Synthesis and Reactions of Organic Compounds. Pub: Pergamon Press (1979), provided that $R^8$ does not include any such moieties that render inoperative the Schemes I and II processes. Reactions to convert $R^8$ to R are performed on products of the synthetic pathways of Schemes I and II or where appropriate or preferable, on certain intermediates in these synthetic pathways. For example, methylthio substituents can be converted to the methylsulfonyl by oxidation. Methoxy substituents can be converted to the hydroxy by treatment with boron tribromide. Hydroxy substituents can be converted to the carboxy by reaction with a trihaloalkylsulfonic anhydride, such as triffuoromethanesulfonic anhydride, followed by a metal catalyzed coupling reaction.

The novel compounds of Formula (II) of the present invention can be prepared by methods outlined in schemes 1–2 below and in the Examples from known and readily available methyl androst-4-en-3-one 17β-carboxylate which has the formula:

Scheme I

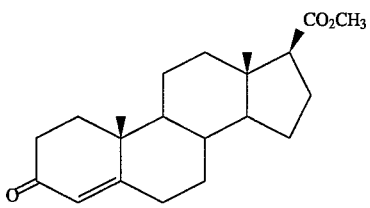

13 14

-continued
Scheme I

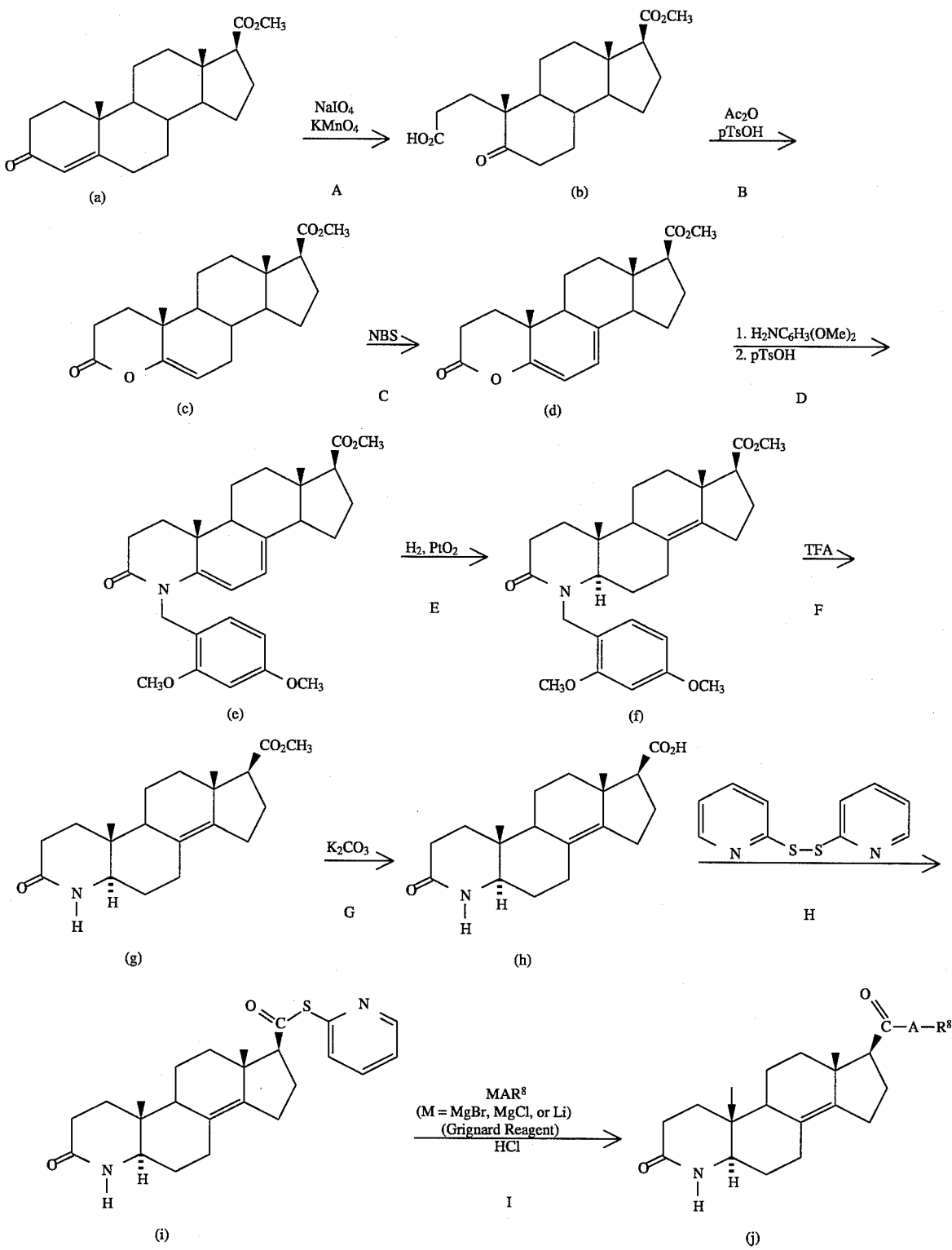

SCHEME I

According to Scheme I, compound (a) is dissolved in a suitable organic solvent such as $C_1$–$C_4$ alkanol, preferably t-butanol, and treated with $Na_2CO_3$ in water. The resulting solution is brought to reflux and treated with ruthenium dioxide/sodium periodate, potassium permanganate, ozone, or, preferably sodium periodiate/potassium permanganate in water followed by acidification to yield a compound of formula (b) (Step A).

Compound (b) is then reacted with p-toluenesulfonic acid monohydrate in acetic anhydride at a temperature of approximately 60° C. to 120° C., preferably 90° C. to prepare a compound of formula (c) (Step B).

The lactone (c) in a suitable organic solvent, such as carbontetrachloride, is reacted with N-bromosuccinimide and epichlorohydrin at an increased temperature, preferably at reflux temperature to yield compound (d) (Step C).

A compound of formula (d) in a suitable organic solvent, such as toluene, is reacted with a benzylamine, preferably a substituted benzylamine, most preferably 2,4-dimethoxybenzylamine, at a temperature of approximately 65° C. to 125° C., preferably 95° C. to form an intermediate which upon heating, preferably to reflux temperature, in a suitable organic solvent, preferably toluene, in the presence of P-toluenesulfonic acid monohydrate with constant water removal yields a compound of formula (e) (Step D).

A compound of formula (f) is prepared from a compound of formula (e) by standard hydrogenation of a compound of formula (e) using hydrogenation agents such as palladium on carbon, Raney nickel, or, preferably platinum dioxide and hydrogenation solvents, such as ethyl acetate, preferably in the presence of an acid, such as acetic acid.

Compound (f) and an acid, preferably trifluoroacetic acid, in an appropriate solvent, preferably dichloromethane, is heated, preferably to reflux, under an inert atmosphere, such as an argon atmosphere, to yield a compound of formula (g) (Step F).

Compound (g) next is reacted with a suitable base, preferably potassium carbonate, then acidified to yield a compound of formula (h) (Step G).

The activated ester (i) is produced (Step H) by treating (h) with 2,2'-dipyridyl disulfide and triphenylphosphine in an appropriate organic solvent solution, such as tetrahydrofuran/toluene, or, preferably dichloromethane, preferably at ambient temperature.

The 17-acyl derivative (j) is produced (Step I) by treating (i) with a Grignard reagent, described hereinbelow, perferably in a tetrahydrofuran or diethyl ether solvent, at a temperature of −50° to −100° C., preferably −78° C.

Scheme II

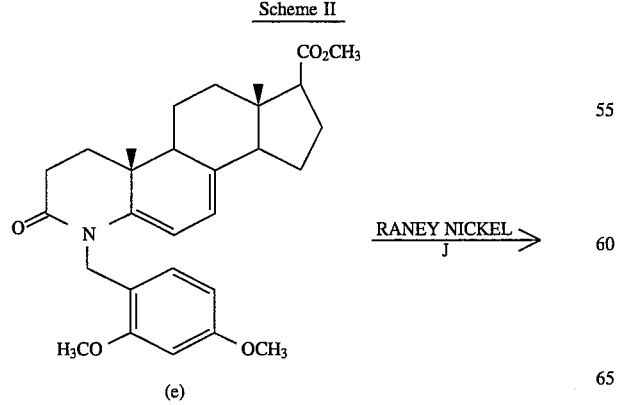

(e)

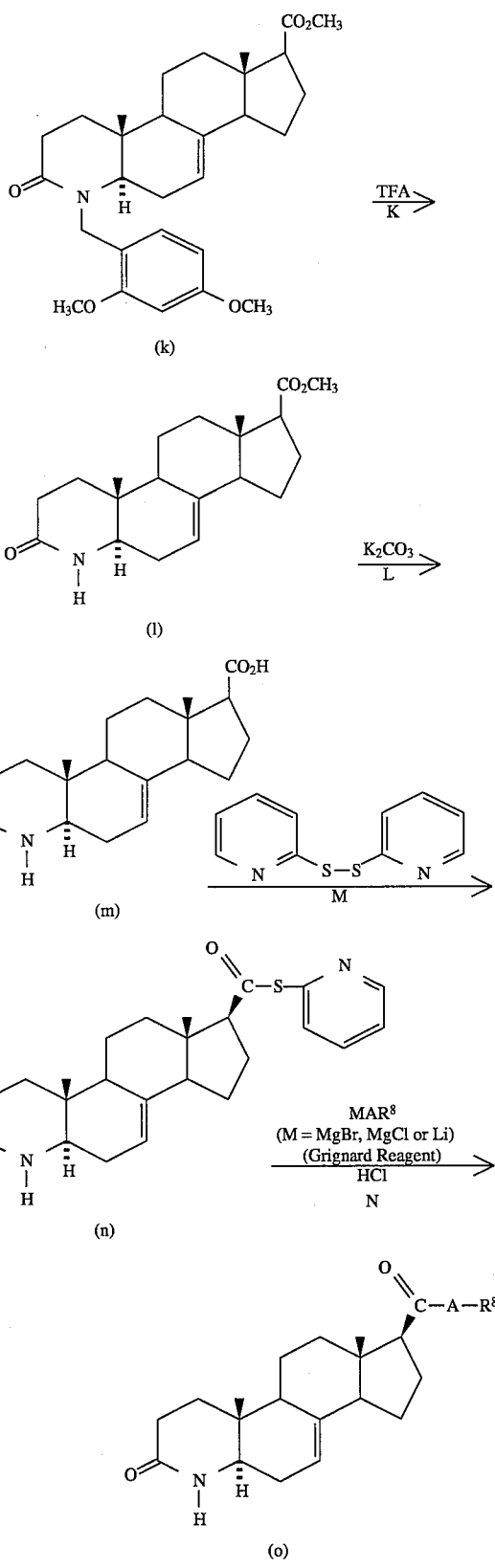

Scheme II outlines formation of formula (I) compounds in which the $C_7$–$C_8$ bond is unsaturated. The starting material for Scheme II is compound (e) from Scheme I. As outlined in Scheme II, a compound of formula (k) is prepared (Step J) by hydrogenation of a compound of formula (e) compound using Raney nickel and close monitoring of the reaction to minimize or prevent formation of a $C_8$–$C_{14}$ double bond.

Compound (k) and an acid, preferably trifluoroacetic acid, in an appropriate solvent, preferably dichloromethane, is heated, preferably to reflux, under an inert atmosphere, such as an argon atmosphere, to yield a compound of formula (1) (Step K).

Compound (1) next is reacted with a suitable base, preferably potassium carbonate, then acidified to yield compound (m) (Step L).

The activated ester (n) is produced (Step M) by treating compound (m) with 2,2'-dipyridyl disulfide and triphenyl phosphine in an appropriate organic solvent solution, such as tetrahydrofuran/toluene, or, preferably dichloromethane, preferably at ambient temperature.

The 17-acyl derivative (o) is produced (Step N) by reacting (n) with a Grignard reagent, described hereinbelow, in a solvent, preferably tetrahydrofuran or diethyl ether, at a temperature of −50° C. to −100° C. preferably −78° C.

As used in Schemes I and II, in the alkylation process (step I and step N respectively), the pyridylthio ester is reacted with an Li-$AR^8$ or an XMgA$R^8$ CX=Cl, Br) Grignard reagent (as described hereinbelow), preferably phenylmagnesium bromide in tetrahydrofuran to form the desired product; preferably 17β-benzoyl-4-aza-5-α-androst-8(14)-en-3-one.

Note that, if $R^8$ is aroyl, which also contains a protected hydroxy group, e.g. with dimethyl-t-butyl-silyl, this may be removed by treating with tetrabutylammonium floride in an appropriate, organic solvent, preferably tetrahydrofuran with a small amount of added acetic acid, at 0° C. reflux for 1–4 hours.

By the term "Grignard reagents" as used in the specification and in the claims is meant compounds of the formula Li-$AR^8$ or XMgA$R^8$ where $R^8$ and X are as used herein.

Grignard reagents of the type, XMg$A^8$, for all of the species included within the scope of this invention, are available or can be made readily by one skilled in the art.

For example, where a $AR^8$ is hydroxyphenyl, this can be derived by starting with an appropriate bromophenol, e.g. p-bromophenol, protecting the phenolic —OH with a conventional blocking group, e.g. triorganosilyl, i.e. t-butyldimethylsilyl, carrying out the Grignard reaction and then deblocking the silyl group by the use of, e.g. refluxing aqueous tetrabutylammonium fluoride.

For $AR^8$ being hydroxyethylphenyl, the same blocking procedure can be analogously conducted starting with the appropriate hydroxyalkyl bromophenol, e.g. p-hydroxymethylbromobenzene, or p-hydroxymethylbromobenzene, or p-hydroxyethylbromobenzene.

Where $AR^8$ is carboxyphenyl, this can be obtained by the chromic acid oxidation of the appropriate hydroxymethylbenzene, e.g. p-bromohydroxymethylbenzene, formed as described above.

Where $AR^8$ is -Oalkyl, the appropriate bromo-Oalkyl benzene, e.g. p-methoxybromobenzene, is utilized for the Grignard reaction.

Other halo substituted benzenes to form the appropriate Grignard reagent useful in the instant invention will be obvious to one skilled in the art from this disclosure.

Formula I compounds in which Z is in the α position are prepared from compounds which contain the corresponding β substituent by the General Method below.

General Method A

To a stirred solution of a substituted 17β steroidal 5α-reductase inhibiting compound of Formula (II) in an appropriate solvent, preferably ethylene glycol or dimethyl sulfoxide, is added a base such as a hydroxide or alkoxide base, preferably sodium hydroxide, potassium hydroxide or sodium methoxide, at a temperature over 100° C. preferably at reflux temperatures to yield the corresponding α epimer, after isolation and work up.

In determining the appropriate solvent for conducting the epimerization, dimethyl sulfoxide or other non-reactive high boiling solvents are preferred when the starting 17β 5α-reductase inhibiting steroidal compound contains reactive substituents or reactive unsaturated bonds that are, for example, subject to nucleophilic attack and ethylene glycol, or other reactive high boiling solvents can be used when the reactivity of the substituents or any unsaturated bonds of the starting 17β 5α-reductase inhibiting steroidal compound is not a consideration.

Also within the scope of the present invention are the ketone reduction products of Formula I compounds, the secondary alcohols of the formula (V):

(V)

[steroid structure with Y substituent]

wherein Y is α or β

$$-\overset{OH}{\underset{|}{C}}-A-R$$

in which A and R are as defined in Formula II, and either the B ring has a double bond where indicated by the broken line or the C ring has a double bond where indicated by the broken line; and pharmaceutically acceptable salts, hydrates and solvates thereof.

Particularly preferred among the presently invented ketone reduction products described above are the secondary alcohols wherein the $$-\overset{OH}{\underset{|}{C}}-A-R$$

substituent is attached in the β position.

These compounds can be made by conventional sodium borohydride reduction of the carbonyl attached to R without epimerization of the $C_{17}$ substituent or reducing the 3-oxo or the $C_7$–$C_8$ or the $C_8$–$C_{14}$ double bond. If the R phenyl contains a carbonyl function, it can be selectively blocked and then regenerated after the borohydride reduction by conventional methods.

The borohydride reduction can be carried out in e.g. water or aqueous methanol, at a temperature of room temperature to 50° C. and the product then isolated and purified by conventional means. The compounds are also active as 5-alpha reductase inhibitors.

By the term "increased temperatures" as used herein and in the claims is meant above 25° C., preferably at reflux temperatures.

By the term "solvent" or "appropriate solvent" as used herein and the in the claims is meant a solvent such as methylene chloride, ethylene chloride, chloroform, ethylene glycol, carbon tetrachloride, tetrahydrofuran (THF), ethyl ether, toluene, ethyl acetate, hexane, dimethylsulfoxide (DMSO), N,N'-dimethyl-N,N'-propylene urea, N-methyl-2-pyrrolidinone, methanol, isopropylalcohol, dimethylformamide (DMF), water, pyridine, quinoline or ethanol.

Pharmaceutically acceptable salts, hydrates and solvates of Formula (I) and Formula (V) compounds are formed, where appropriate, by methods well known to those of skill in the art.

In preparing the presently invented compounds of Formula (II), novel intermediates of the following Formula (IV) are synthesized;

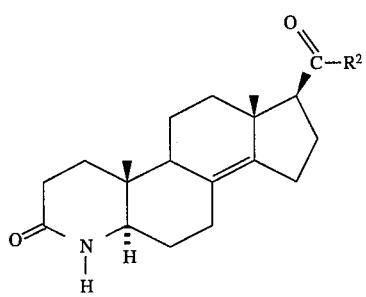

in which $R^2$ is 2-thiopyridyl.

A preferred process for preparing a compound of Formula (III)

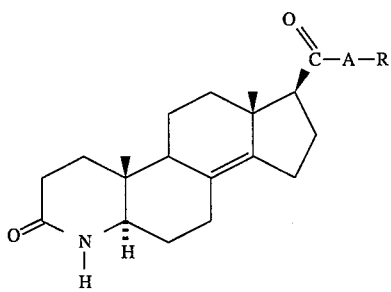

in which A and R are as defined above and pharmaceutically acceptable salts, hydrates and solvates thereof comprises reacting a compound of the formula

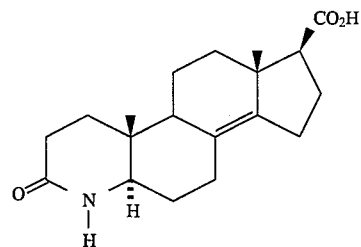

with 2,2'-dipyridyl disulfide and triphenylphosphine in a solvent, preferably dichloromethane, to form a compound of the formula

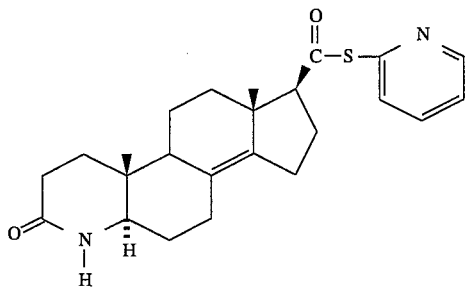

and subsequently reacting said compound with a Grignard reagent, as defined herein, in a solvent, preferably tetrahydrofuran or diethylether, to form a compound of the formula

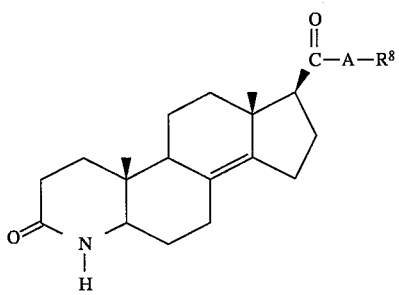

in which A and $R^8$ are as described above and optionally, if applicable, converting $R^8$ to R and thereafter optionally forming a pharmaceutically acceptable salt, hydrate or solvate thereof.

Because the presently invented pharmaceutically active compounds inhibit steroid 5-α-reductase activity, they have therapeutic utility in treating diseases and conditions wherein decreases in DHT activity produces the desired therapeutic effect. Such diseases and conditions include ache vulgaris, seborrhea, female hirsutism, male pattern baldness, prostate diseases such as benign prostatic hypertrophy, and prostatic adenocarcinoma.

In determining potency in inhibiting the human 5α-reductase enzyme, the following procedure was employed:

Preparation of membrane particulates used as source for recombinant steroid 5α-reductase isozyme 1.

Chinese hamster ovary (CHO) cells containing expressed, recombinant human steroid 5α-reductase isoenzyme 1 (Andersson, S., Berman, D. M., Jenkins, E. P., and Russell, D. W. (1991) Nature 354 159–161) were homogenized in 20 mM potassium phosphate, pH 6.5, buffer containing 0.33M sucrose, 1 mM dithiothreitol, and 50 μM NADPH (buffer A) using a Dounce glass-to-glass hand homogenizer (Kontes Glass Co., Vineland, N.J.). Membrane particulates were isolated by centrifugation (100,000×g at 4° C. for 60 minutes) and resuspended in 20 mM potassium phosphate, pH 6.5, containing 20% glycerol, 1 mM dithiothreitol, and 50 μM NADPH (buffer B). The suspended particulate solution was stored at −80° C.

Preparation of prostatic membrane particulates used as source for steroid 5α-reductase isozyme 2.

Frozen human prostates were thawed and minced into small pieces (Brinkmann Polytron (Sybron Corp., Westbury, N.Y.). The solution was sonicated for 3 to 5 minutes with a Sonifier (Branson Sonic Power Co.) followed by hand homogenization in a Dounce hand homogenizer. Prostatic particles were obtained by differential centrifugation at 600 or 1000×g for 20 minutes, and 140,000×g for 60 minutes at 4° C. The pellet obtained from the 140,000×g centrifugation was washed with 5 to 10 tissue volumes of the buffer described above and centrifuge d at 140,000×g. The resulting pellet was suspended in buffer B and the particulate suspension was stored at −80° C.

Preparation of membrane particulates used as source for recombinant steroid 5-α-reductase isozyme 2.

Chinese hamster ovary (CHO) cells containing expressed, recombinant human steroid 5-α-reductase isozyme 2 were homogenized in 20 mM potassium phosphate, pH 6.5, buffer containing 0.33M sucrose, 1 mM dithiothreitol, and 50 μM NADPH (buffer A) using a Douce hand homogenizer. Membrane particulates containing the recombinant human enzyme were isolated by centrifugation (100,000×g at 4° C. for 60 minutes) and resuspended in 20 mM potassium phosphate, pH 6.5 containing 20% glycerol, 1 mM dithiothreitol, and 50 μM NADPH (buffer B). The suspended particulate solution was stored at −80° C. until used.

Assay for enzymes activities and inhibitors potency.

A constant amount of [$^{14}$C]testosterone (50 to 55 mCi/mmol) in ethanol and varying amounts of potential inhibitor in ethanol were deposited in test tubes and concentrated to dryness in vacuo. To each tube was added buffer, 10 μL (recombinant isoenzyme I or isoenzyme 2) or 20 μL (isoenzyme 2 from human prostate tissue) of 10 mM NADPH and an aliquot of asteroid 5α-reductase preparation to a final volume of 0.5 mL. Assays for human steroid 5α-reductase isoenzyme 1 were conducted with a sample of the recombinant protein expressed in CHO cells in 50 mM phosphate buffer, pH 7.5 while assays of isoenzyme 2 were conducted with a suspension of human prostatic particulates and/or recombinant protein expressed in CHO cells in 50 mM citrate buffer at pH 5.0.

After incubating the solution at 37° C. for 20 or 30 minutes the reaction was quenched by the addition of 4 mL ethyl acetate and 0.25 μmol each of testosterone, 5α-dihydrotestosterone, androstanediol, and androstanedione as carriers. The organic layer was removed to a second test tube and evaporated to dryness in a Speed Vac. The residue was dissolved in 40 μL chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan Inc., Washington, D.C.). The percent of recovered radiolabel converted to product was calculated, from which enzyme activity was determined. All incubations were conducted such that no more than 20% of the substrate (testosterone) was consumed.

The experimentally obtained data was computer fit to a linear function by plotting the reciprocal of the enzyme activity (1/velocity) against the variable inhibitor concentration; apparent inhibition constants ($K_{i,app}$) were determined by the Dixon analysis (Dixon, M. (1953).

The value for the inhibition constant (Ki) was calculated from known procedures (Levy, M. (1989), Biochemistry, 29:2815–2824).

All of the compounds within the scope of this invention are useful in inhibiting steroid 5-α-reductase in a mammal, including humans, in need thereof.

A compound within the scope of this invention has been tested and has shown an activity of 5 Ki(nM) against isozyme 1 and an activity of 50 Ki(nM) against isozyme 2. Particularly preferred among the compounds of the invention and the compounds used in the invented pharmaceutical compositions and invented methods is 17β-benzoyl-4-aza-5-α-androst 8(14)-en-3-one.

The pharmaceutically active compounds of the present invention are preferably incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will preferably be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.1–1000 mg/kg of active compound, preferably 1–100 mg/kg. When treating a human patient in need of steroid 5-α-reductase inhibition, the selected dose is administered preferably from 1–6 times daily, orally or parenterally. Preferred forms of parenteral administration include topically, rectally, transdermally, by injection and continuously by infusion. Oral dosage units for human administration preferably contain from 1 to 500 mg of active compound. Oral administration, which uses lower dosages is preferred. Parenteral administration, at high dosages, however, also can be used when safe and convenient for the patient.

The method of this invention of inhibiting steroid 5-α-reductase activity in mammals, including humans, comprises administering to a subject in need of such inhibition an effective steroid 5-α-reductase inhibiting amount of a pharmaceutically active compound of the present invention.

The invention also provides for the use of a compound of Formula (I) or a compound of Formula (V) in the manufacture of a medicament for use in the inhibition of steroid 5-α-reductase.

The invention also provides for a pharmaceutical composition for use in the treatment of benign prostate hypertrophy which comprises a compound of Formula I or a compound of Formula (V) and a pharmaceutically acceptable carrier.

The invention also provides for a pharmaceutical composition for use in the treatment of prostatic adenocarcinoma which comprises a compound of Formula I or a compound of Formula (V) and a pharmaceutically acceptable carrier.

The invention also provides for a process for preparing a pharmaceutical composition containing a pharmaceutically acceptable carrier or diluent and a compound of Formula I or a compound of Formula (V) which comprises bringing the compound of Formula I or the compound of Formula (V) into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat the disease states of acne vulgaris, seborrhea, female hirsutism, male pattern baldness, benign prostate hypertrophy or prostatic adenocarcinoma or compounds known to have utility when used in combination with 5-α-reductase inhibitors. Particularly preferred is the co-administration of a 5-α-reductase inhibitor, as disclosed herein, and minoxidil for use in the treatment of male pattern baldness. Particularly preferred is the co-administration of a 5α-reductase inhibitor, as disclosed herein, and a α-receptor antagonist for use in the treatment of benign prostatic hypertrophy. Preferred is the co-administration of a 5-α-reductase inhibitor, as disclosed herein, and an aromatase inhibitor for use in the treatment of benign prostatic hypertrophy. Preferred is the co-administration of a 5-α -reductase inhibitor, as disclosed herein, a α-receptor antagonist and an aromatase inhibitor for use in the treatment of benign prostatic hypertrophy.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1—Corresponding to Scheme I
17β-Benzoyl-4-aza-5α-androst-8(14)-ene-3-one (i) 17β-(Carbomethoxy)-5-oxo-3,5-seco-androst-3-oic Acid.

To a stirred solution of methyl androst-4-en-3-one 17β-carboxylate (12 g, 36 mmol) in 200 mL oft-butanol was added a solution of $Na_2CO_3$ (5.6 g, 52.8 mmol) in water (40 mL). The mixture was brought to reflux and a solution of $NaIO_4$ (53 g, 250 mmol) and $KMnO_4$ (0.42 g, 2.7 mmol) in warm water (200 mL, 75° C.) was added gradually as the reflux was maintained. Following the completion of the addition, the mixture was heated at reflux for 2 h and then cooled to 30° C. After 15 min, the solids were removed by filtration. The solids were washed with water and the combined filtrates were concentrated in vacuo. The residual aqueous mixture was cooled in an ice water bath and acidified with concentrated aqueous HCl to pH 3. The product was extracted with dichoromethane, washed with water, dried, and concentrated to a white foam (12.7 g). Trituration with diethyl ether provided the title compound as a white solid, mp 160° C.

(ii) Methyl 4-Oxa-androst-5-en-3-one-17β-carboxylate.

A mixture of 17β-(carbomethoxy)-5-oxo-3,5-seco-androst-3-oic acid (12.6 g, 36 mmol), acetic anhydride (126 mL), and p-toluenesulfonic acid monohydrate (1.26 g) was heated for 3 h at 90° C. The volatiles were then removed in vacuo. The soft white solid residue was dissolved in diethyl ether, washed rapidly with aqueous $NaHCO_3$, brine, dried ($MgSO_4$), and concentrated. The gummy residue was triturated with hexanes-ethyl acetate (ca. 95:5) to provide the title lactone (8.2 g) as a white solid, mp. 156°–159° C. Chromatography of the trituration mother liquor (silica gel eluting with 1:3 ethyl acetate-hexanes), followed by recrystallization from ethyl acetate-hexane provided an additional 1.5 g of product.

(iii) Methyl 4-Oxa-androst-5,7-dien-3-one-17β-carboxylate.

A mixture of methyl 4-oxa-androst-5-en-3-one-17β-carboxylate (13.8 g, 41.6 mmol), N-bromosuccinimide (8.35 g, 47 mmol), and epichlorohydrin (13.8 mL) in carbon tetrachloride (800 mL) was heated at reflux for 18 h. The reaction mixture was cooled and filtered, and the filtrate evaporated. Chromatography of the residue (silica gel, eluting with 3:7 ethyl acetate-hexanes) followed by recrystallization from ethyl acetate-hexane provided 6.4 g of the title compound, mp. 152° C. (softens 130° C.).

(iv) Methyl 4-(2,4-Dimethoxybenzyl)-4-aza-androst-5,7-dien-3-one- 17β-carboxylate.

A mixture of methyl 4-oxa-androst-5,7-dien-3-one-17β-carboxylate (5.0 g, 15 mmol) and 2,4-dimethoxtbenzylamine (3.5 g, 17 mmol) in toluene (500 mL) was heated at 95° C. for 1.25 h. The reaction mixture was then concentrated in vacuo and the residue was chromatographed (silica gel, eluting with 1:1 ethyl acetate-hexanes) to provide 7.5 g of a white foam intermediate. The intermediate was dissolved in toluene (500 mL) and heated at reflux for 1.25 h in the presence of a trace amount of p-toluenesulfonic acid monohydrate and using a Dean-Stark trap for azeotropic removal of water. The cooled reaction mixture was washed with water, dried, and evaporated. Chromatography of the residue (silica gel, eluting with 35:65 ethyl acetate-hexane) provided the title compound as a white foam (6.4 g).

(v) Methyl 4-(2,4-Dimethoxybenzyl)-4-aza-5a-androst-8(14)-en-3-one- 17β-carboxylate.

A solution of methyl 4-(2,4-dimethoxybenzyl)-4-aza-androst-5,7-dien-3-one- 17β-carboxylate (0.9 g, 1.9 mmol) in acetic acid-ethyl acetate (1:9, 100 mL) was stirred over $PtO_2$ (300 mg) under an atmosphere of hydrogen for 2.5 h. The catalyst was removed by filtration and the filtrate was evaporated in vacuo to provide the title compound as a white foam (0.9 g).

(vi) Methyl 4-Aza-5a-androst-8(14)-en-3-one-17β-carboxylate.

A solution of methyl 4-(2,4-dimethoxybenzyl)-4-aza-5a-androst-8(14)-en 3-one-17β-carboxylate (0.8 g, 1.66 mmol) in dichloromethane (15 mL) was treated with trifluoroacetic acid (3.5 mL) and heated to a very gentle reflux for 15 min under an argon atmosphere and then allowed to stand at ambient temperature overnight. The resulting dark-pink solution was concentrated in vacuo. The residue was then dissolved in dichloromethane, washed with 5% aqueous $NaHCO_3$, and brine, dried, and concentrated to a white powder. Trituration with diethyl ether provided 0.3 g of the title compound.

(vii) 4-Aza-5a-androst-8(14)-en-3-one-17β-carboxylic Acid.

A mixture of methyl 4-aza-5a-androst-8(14)-en-3-one-17β-carboxylate (0.3 g, 1 mmol), $K_2CO_3$ (0.5 g, 3.6 mmol), water (5 mL) and methanol (50 mL) was heated at reflux overnight. The reaction mixture was then filtered and the filtrate was concentrated. The residue was diluted with water and the aqueous solution was washed with ethyl acetate. The aqueous layer was then acidified with dilute HCl and the resulting white precipitate was isolated by filtration, washed with water, and triturated with acetone to provide the title compound (0.23 g) as a white solid, top.

(viii) S-(2-Pyridyl)-4-aza-5a-androst-8(14)-en-3-one-17β-thiocarboxylate.

A mixture of 4-aza-5a-androst-8(14)-en-3-one- 17β-carboxylic acid (0.21 g, 0.66 mmol), 2,2'-dipyridyl disulfide (0.29 g, 1.32 mmol), triphenylphosphine (0.35 g, 1.34 mmol) and dichloromethane (50 mL) was stirred at ambient temperature under argon overnight. The resulting solution was concentrated and the residue was chromatographed (silica gel, eluting with 2% methanol in ethyl acetate) to provide 0.19 g of the title compound, mp. 241°–243° C. (recrystallized from methanol).

(ix) 17β-Benzoyl-4-aza-5a-androst-8(14)-en-3-one.

Phenylmagnesium bromide solution (0.55 mL; 1M in diethyl ether) was added slowly to a suspension of S-(2-pyridyl)-4-aza-5a-androst-8(14)-en 3-one-17β-thiocarboxylate (62 mg, 0.15 mmol)in tetrahydrofuran (10 mL) at −78° C. After 30 min, the mixture was warmed to −10° C. and stirred for an additional 30 min during which time the mixture became homogeneous. The reaction solution was quenched with saturated aqueous NH$_4$Cl and thoroughly extracted with ethyl acetate. The organic extract was washed with brine, dried, and concentrated. The resulting residue was chromatographed (silica gel, eluting with 2% methanol in ethyl acetate) to provide 35 mg of the title compound as a white solid, top. 290°–295° C. (after diethyl ether trituration).

EXAMPLE 2—CORRESPONDING TO SCHEME II

17β-Benzoyl-4-aza-5α-androst-7-ene-3-one (i) Methyl 4-(2,4-Dimethoxybenzyl)-4-aza-androst-5,7-dien-3-one- 17β-carboxylate.

The title compound prepared according to Example 1 (i–iv).

(ii) Methyl 4-(2,4-Dimethoxybenzyl)-4-aza-5α-androst-7-en-3-one- 17β-carboxylate.

A solution of methyl 4-(2,4-dimethoxybenzyl)-4-aza-androst-5,7-dien-3-one- 17β-carboxylate in ethyl acetate is stirred over Raney nickel under an atmosphere of hydrogen with close monitoring to minimise or prevent the formation of an 8(14) double bond. The catalyst is removed by filtration and the filtrate is evaporated in vacuo to provide the title compound.

(iii) Methyl 4-Aza-5α-androst-7-en-3-one-17β-carboxylate.

A solution of methyl 4-(2,4-dimethoxybenzyl)-4-aza-5α-androst-7-en-3-one- 17β-carboxylate in dichloromethane is treated with trifluoroacetic acid and heated to a very gentle reflux for 15 min under an argon atmosphere and then allowed to stand at ambient temperature overnight. The resulting dark-pink solution is concentrated in vacuo. The residue is then dissolved in dichloromethane, washed with 5% aqueous NaHCO$_3$, and brine, dried, and concentrated. Trituration with diethyl ether provides the title compound.

(iv) 4-Aza-5α-androst-7-en-3-one-17β-carboxylic Acid.

A mixture of methyl 4-aza-5α-androst-7-en-3-one- 17β-carboxylate K$_2$CO$_3$ water and methanol is heated at reflux overnight. The reaction mixture is then filtered and the filtrate is concentrated. The residue is diluted with water and the aqueous solution is washed with ethyl acetate. The aqueous layer is then acidified with dilute HCl and the resulting white precipitate is isolated by filtration, washed with water, and triturated with acetone to provide the title compound (0.23 g) as a white solid, mp.

(v) S-(2-Pyridyl)-4-aza-5α-androst-7-en-3-one-17β-thiocarboxylate.

A mixture of 4-aza-5α-androst-7-en-3-one-17β-carboxylic acid 2,2'-dipyridyl disulfide triphenylphosphine and dichloromethane is stirred at ambient temperature under argon overnight. The resulting solution is concentrated and the residue is chromatographed (silica gel) to provide the title compound.

(vi) 17β-Benzoyl-4-aza-5α-androst-7-en-3-one.

Phenylmagnesium bromide solution 1M in diethylether is added slowly to a suspension of S-(2-pyridyl)-4-aza-5α-androst-7-en-3-one-17β-thiocarboxylate in tetrahydrofuran at −78° C. After 30 min, the mixture was warmed to −10° C. and stirred for an additional 30 min during which time the mixture becomes homogeneous. The reaction solution is quenched with saturated aqueous NH$_4$Cl and thoroughly extracted with ethyl acetate. The organic extract is washed with brine, dried, and concentrated. The resulting residue is chromatographed to provide the title compound.

EXAMPLE 3

An oral dosage form for administering Formula I comounds is produced by screening, mixing, and filling into hard gelatin capsules the ingredients in the proportions shown in Table 1, below.

TABLE I

| Ingredients | Amounts |
| --- | --- |
| 17β-Benzoyl-4-aza-5-α-androst-8(14)-ene-3-one | 50 mg |
| magnesium stearate | 5 mg |
| lactose | 75 mg |

EXAMPLE 4

The sucrose, calcium sulfate dihydrate and Formula (I) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 17β-Benzoyl-4-aza-5-α-androst-8(14)-ene-3-one | 100 mg |
| calcium sulfate dihydrate | 150 mg |
| sucrose | 20 mg |
| starch | 10 mg |
| talc | 5 mg |
| stearic acid | 3 mg |

EXAMPLE 5

17β-Benzoyl-4-aza-5-α-androst- 8(14)-ene-3-one, 75 mg, is dispursed in 25 ml of normal saline to prepare an injectable preparation.

While the preferred embodimetns of the invention are illustrated by the above, it is to be understood that the invention is not limited to the precise instructions herein disclosed and that the right to all modifications comming within the scope of the following claims is reserved.

What is claimed is:

1. A compound represented by the formula:

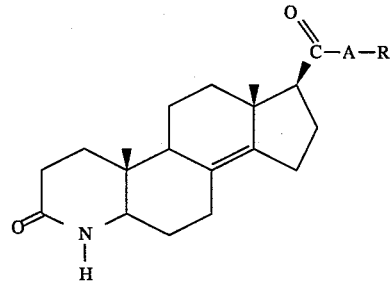

in which A is absent or present as a linear or branched, saturated or unsaturated hydrocarbon chain having from 1–4 carbon atoms and R is a) $C_3$–$C_8$ nonaromatic, unsaturated or saturated cycloalkyl, optionally substituted with one substituent selected from the group consisting of: halogen, thio, methylsulfonyl, methylsulfoxyl, methylthio, carboxy, hydroxy, trifluoromethyl, phenoxy and methoxy or b) $C_6$–$C_{12}$ aryl, optionally substituted with one substituent selected from the group consisting of: thio, methylsulfonyl, methylsulfoxyl, methylthio, carboxy, hydroxy, trifluoromethyl, phenoxy and methoxy and pharmaceutically acceptable salts, hydrates and solvates thereof.

2. A compound of claim 1 wherein A is absent or present as a linear or branched, saturated or unsaturated hydrocarbon chain having from 1–4 carbon atoms and R is a) $C_5$–$C_7$ cycloalkyl or b) $C_6$–$C_{12}$ aryl, optionally substituted with one substituent selected from the group consisting of: thio, methylsulfonyl, methylsulfoxyl, methylthio, carboxy, hydroxy, trifluoromethyl, phenoxy and methoxy and pharmaceutically acceptable salts, hydrates and solvates thereof.

3. A compound of claim 2 which is 17β-benzoyl-4-aza-5-α-androst-8(14) ene-3-one or a pharmaceutically acceptable salt, hydrate of solvate thereof.

4. A pharmaceutical composition for inhibiting testosterone 5-alpha reductase which comprises a pharmaceutically acceptable carrier and an effective amount of a compound of claim 1.

5. A method of inhibiting steroid 5-α-reductase which comprises administration to a patient in need of such treatment a therapeutically effective amount of a compound of claim 1.

* * * * *